United States Patent [19]

Langham

[11] 4,147,785
[45] Apr. 3, 1979

[54] METHOD FOR THE TREATMENT OF ONCHOCERCIASIS

[75] Inventor: Maurice E. Langham, Lutherville, Md.

[73] Assignee: Graham J. Dobbie, Chicago, Ill.; a part interest

[21] Appl. No.: 779,145

[22] Filed: Mar. 18, 1977

[51] Int. Cl.² ............................................. A61K 31/495
[52] U.S. Cl. ...................................................... 424/250
[58] Field of Search ......................................... 424/250

[56] References Cited
FOREIGN PATENT DOCUMENTS 2537202  3/1976  Fed. Rep. of Germany ............ 424/250

Primary Examiner—Jerome D. Goldberg

[57] ABSTRACT

Helmintic infections such as filariasis are effectively treated by topical application of a composition which comprises a dermatologically acceptable inert carrier suitable for application to human skin and having dispersed therein an anthelmintically effective but non-toxic quantity of a piperazine derivative having the general formula

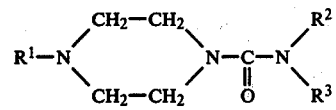

or a corresponding physiologically tolerable acid addition salt thereof. In the foregoing formula, $R^1$ can be hydrogen or an alkyl radical containing 1 to 8 carbon atoms, and $R^2$ and $R^3$ can be alike or different and are members of the group consisting of hydrogen and alkyl radicals containing 1 to 8 carbon atoms with the proviso that at least one of the $R^2$ and $R^3$ groups is an alkyl radical.

11 Claims, 6 Drawing Figures

METHOD FOR THE TREATMENT OF ONCHOCERCIASIS

BACKGROUND OF THE INVENTION

This invention relates to a composition and method for treating helmintic infections. In one aspect, this invention is directed to the treatment of filarial infections.

Infestations with filarial helminths, such as the species *Wucheria bancrofti, Onchocerca volvulus* and the like, are quite common in West and Central Africa and in South and Central America. Similar species of filariae are also found in India, southern China, on the islands of Western Pacific, and in other regions. Studies have revealed that a major portion of the people living in the endemic areas of the foregoing regions are infected with these parasitic worms. Moreover, as a result of increased mobility of the people and the ease of air travel to and from regions where such parasitic infestations are endemic, these parasites may be transported by infected persons to, and may appear in, countries where they previously had been unknown.

One such filarial worm, *Onchocerca volvulus*, is very common all over West and Central Africa, and is believed to have been imported from there into Mexico, northeastern Venezuela, and Guatemala. The disease resulting from an infestation of this particular species, onchocerciasis, is a vector-borne disease that is transmitted via an insect bite. For example, infective larvae of this species can be introduced into the human body by the bite of the female black fly *Simulium damnosum*. The inoculated male and female larvae thereafter mature into worms which give rise to large numbers of microfilariae. The latter move freely through the dermal connective tissue of the infected individual and usually remain close to the skin surface in all regions of the human body. The biological cycle of *O. volvulus* is completed upon a subsequent uptake of microfilariae during an insect bite back into the insect vector where the microfilariae develop into infective larvae.

The most serious manifestations of this human disease are eye lesions which account for a high incidence of visual impairment and blindness in the endemic areas. Invasion of the corneal connective tissue by the microfilariae and their subsequent death leads to multiple discrete opacities and, in severe cases, to complete corneal opacification. In endemic regions where the intensity of the disease is particularly severe and where corneal opacification is extremely common, blindness due to onchocerciasis affects about 10 to about 30 percent of the population. In regions where the intensity of the disease is less severe and corneal opacification is less common, nevertheless onchocerciasis is associated with a high incidence of glaucoma in all age groups (including adolescents) and results in an incidence of blindness in about 10 percent of the population.

Elimination of onchocerciasis depends on either complete eradication of the infected insect vector or the destruction of the parasite in the human body. The vector control program initiated by the Word Bank and the World Health Organization has opted to pursue the former approach to control this disease in the Upper Volta basin; however, the program is very costly and the likelihood of its success is difficult to predict. The latter approach heretofore has utilized chemotherapy based on the oral administration of substantial doses of N,N-diethyl-4-methylpiperazine-1-carboxamide dihydrogen citrate (diethylcarbamazine or DEC).

However, such chemotherapy has considerable drawbacks inasmuch as the initial systemic reactions provoked by massive destruction of the microfilariae present may be quite severe and may require the administration of antihistamines or, in very severe cases, corticosteroids. In addition, observed side effects that are believed to be directly associated with the oral administration of diethylcarbamazine include headache, general malaise, weakness, joint pains, anorexia, nausea, and vomiting. Other untoward responses also have been reported. For example, in patients with onchocerciasis there is usually a violent reaction within about 16 hours after administration of the first oral dose. This reaction includes swelling and edema of the skin, intense itching, enlargement and tenderness of the inguinal lymph nodes, sometimes a fine papular rash, hyperpyrexia up to 102° F., tachychardia and headache. These symptoms can persist for about 3 to about 7 days, and, of course, have a debilitating effect on the patient.

The foregoing untoward side effects notwithstanding, diethylcarbamazine has been widely used as an oral chemotherapeutic against filarial infections since the late 1940's. When orally administered daily for a period of several weeks, diethylcarbamazine decreases the skin count of the microfilariae of *O. volvulus* to very low levels. However, such a treatment fails to kill the parent parasitic worm, and cessation of the oral chemotherapy results in a rapid resurgence of microfilarial density in the skin.

Accordingly, there exists a need for a more effective treatment of helmintic infections, in particular of onchocerciasis, and for means to effect such treatment.

SUMMARY OF THE INVENTION

The present invention contemplates a transdermal application of an active ingredient in human patients infected with or susceptible to a helmintic infection.

A topical composition for the treatment of helmintic infections comprises a dermatologically acceptable inert carrier suitable for application to human skin and having dispersed therein an anthelmintically effective but non-toxic quantity of a certain piperazine derivative. The contemplated piperazine derivative can be a compound having the general formula wherein $R^1$ is hydrogen or an alkyl radical containing 1 to 8 carbon atoms, and $R^2$ and $R^3$ can be alike or different and are hydrogen or an alkyl radical containing 1 to 8 carbon atoms. However, in all instances at least one of the $R^2$ and $R^3$ groups has to be an alkyl radical. The corresponding physiologically tolerable acid addition salts of the foregoing piperazine derivatives are also suitable. Preferably, the piperazine derivative is dispersed in the carrier in an amount of about 0.1 to about 5 percent by weight.

The presently contemplated treatment of helmintic infection, e.g., a filarial infection, comprises topical administration of an anthelmintic amount of a piperazine derivative characterized hereinabove. Preferably, the amount of the piperazine derivative that is administered in such that about 0.05 to about 0.25 micrograms (μg) of the piperazine derivative are provided per square millimeter of the patient's skin in the area of application.

DESCRIPTION OF PREFERRED EMBODIMENTS

The piperazine derivatives contemplated as the active ingredients in the compositions of the present invention are known in the art, and can be represented by the general formula wherein $R^1$ is hydrogen or an alkyl radical containing 1 to 8 carbon atoms (preferably 1 to 4 carbon atoms), and $R^2$ and $R^3$ can be alike or different and are hydrogen or alkyl radicals containing 1 to 8 carbon atoms (preferably 1 to 4 carbon atoms), with the further proviso that at least one of the $R^2$ and $R^3$ groups is an alkyl radical.

These piperazine derivatives can be prepared by reacting piperazine or an N-alkyl piperazine with the appropriate substituted carbamyl chloride at a temperature of about 32° F. (0° C.) to about 104° F. (40° C.) and in a suitable solvent such as chloroform, carbon tetrachloride, ethyl acetate, water, or the like. The compounds and their preparation are disclosed in detail in U.S. Pat. No. 2,467,893 to Kushner et al. and in U.S. Pat. No. 2,467,895 to Kushner et al.

The foregoing compounds can exist in the non-protonated or free base form as depicted above, or in the protonated or acid addition salt form, depending on the pH of the environment therefor. The acid addition salt form, provided this form is physiologically tolerable, can also be utilized in practicing the present invention.

Acid addition salts of the foregoing compounds can be prepared by the neutralization of the free base form with an appropriate amount of an organic or inorganic acid, examples of which are hydrochloric, hydrobromic, phosphoric, acetic, lactic, salicylic, glycolic, succinic, tartaric, maleic, malic, pamoic, citric, and the like. The neutralization can be carried out by a variety of procedures known to the art to be generally useful for the preparation of amine acid addition salts. The choice of the most suitable procedure will depend on a variety of factors including convenience of operation, economic considerations, and particularly the solubility characteristics of the particular free base, the acid, and the acid addition salt.

For example, if the acid is soluble in water, the free base can be dissolved in water containing an equivalent amount of the acid, and thereafter, the water can be removed by evaporation; in some instances, the salt precipitates from the aqueous solution, particularly when cooled, and evaporation is not necessary. If the acid is soluble in a relatively non-polar solvent, for example, diethyl ether or diisopropyl ether, separate solutions of the acid and free base is such a solvent can be mixed in equivalent amounts, whereupon the acid addition salt will usually precipitate because of its relatively low solubility in the non-polar solvent. Alternatively, the free base can be mixed with an equivalent amount of the acid in the presence of a solvent of moderate polarity, for example, a lower alkanol, a lower alkanone, or a lower-alkyl ester of a lower alkanoic acid. Examples of these solvents are ethanol, acetone, and ethyl acetate, respectively. Subsequent admixture of the resulting solution of acid addition salt with a solvent of relatively low polarity, for example, diethyl ether or hexane, will usually cause precipitation of the acid addition salt. These acid addition salts are also useful for upgrading the free bases.

Illustrative N,N-disubstituted compounds that can be used for the treatment of filariasis in accordance with the present invention are the following:

N,N-diethyl-4-methylpiperazine-1-carboxamide
N,N-dimethyl-4-methylpiperazine-1-carboxmide
N,N-dimethyl-piperazine-1-carboxamide
N,N-diethyl-piperazine-1-carboxamide
N,N-dipropyl-piperazine-1-carboxamide
N,N-diethyl-4-ethylpiperazine-1-carboxamide
N,N-dipropyl-4-methylpiperazine-1-carboxamide
N,N-diisopropyl-4-methylpiperazine-1-carboxamide
N,N-diethyl-4-isoproylpiperazine-1-carboxamide
N,N-diisopropyl-4-isopropylpiperazine-1-carboxamide
N,N-dibutyl-4-methylpiperazine-1-carboxamide
N,N-ditertiarybutyl-4-methylpiperaine-1-carboxamide
N,N-diamyl-4-ethylpiperazine-1-carboxamide
N,N-diethyl-4-butylpiperazine-1-carboxamide
N,N-diethyl-4-octylpiperazine-1-carboxamide Similarly, illustrative N-substituted compounds that can be used for the treatment of filariasis are the following:

N-ethyl-4-methylpiperazine-1-carboxamide
N-methyl-4-methylpiperazine-1-carboxamide
N-propyl-4-methylpiperazine-1-carboxamide
N-isopropyl-4-methylpiperazine-1-carboxamide
N-hexyl-4-isopropylpiperazine-1-carboxamide
N-amyl-4-ethylpiperazine-1-carboxamide
N-octyl-4-methylpiperazine-1-carboxamide For the treatment of onchocerciasis, particularly preferred as the chemotherapeutic agent are N,N-diethyl-4-methylpiperazine-1-carboxamide, the citric acid addition salt thereof, i.e., N,N-diethyl-4-methylpiperazine-1-carboxamide dihydrogen citrate, and the hydrochloric acid addition salt thereof, i.e., N,N-diethyl-4-methylpiperazine-1-carboxamide hydrochloride. Both the citrate salt and the hydrochloride salt are very soluble in water, thus aqueous solutions thereof can be readily utilized per se, or in wet dressings that are applied to the skin. The chemotherapeutic agent can also be applied to the skin in the form of a lotion, as an ointment, as an aerosol spray, or in any other convenient manner.

In the compositions of the present invention, an anthelmintically effective but non-toxic quantity of the hereinabove characterized piperazine derivative is dispersed in a dermatologically acceptable inert carrier that is suitable for application to human skin, i.e., suitable for topical or external application. The carrier can be water, an oil-in-water emulsion, an aqueous solution of glycerin, an aqueous solution of propylene glycol, an aqueous solution of polyethylene glycol, dimethylsulfoxide (DMSO), collodion, flexible collodion, pyroxylon (5%) in an ether-alcohol vehicle, zinc gelatin, dimethicone, and the like.

Also suitable are oleaginous, absorption, emulsion, and water-soluble ointment bases as defined and described in Sollman, *A Manual of Pharmacology*, W. B. Saunders Co., Philadelphia, Pa. (1957) on page 10. Illustrative of such ointment bases are lard, petrolatum, hydrogenated unsaturated vegetable oils, anhydrous lanolin, cold cream, and the like. Other illustrative vehicles are the commercially-available skin care lotions.

The compositions are compounded by admixing the piperazine derivative with the carrier in any convenient manner to provide the desired concentration of the piperazine derivative. Preferably the carrier contains about 0.1 to about 5 percent by weight of the piperazine derivative, more preferably about 0.75 to about 1.25 percent by weight. A particularly preferred concentration is about 1 percent by weight.

The composition can also contain an insect repellent, e.g., citronella oil, or an agent enhancing skin permeability such as DMSO or a cationic surface-active agent, e.g., a 0.01% to 0.03% benzalkonium chloride solution.

In treating a human patient afflicted with a filarial infection, the present composition is administered topically as a lotion, an ointment, an aerosol spray, a wet dressing, or the like, to provide a filaricidal but non-toxic quantity of piperazine derivative on the patient's skin. Preferably about 0.05 to about 0.25 micrograms, more preferably about 0.1 micrograms of the piperazine derivative per square millimeter of the patient's skin in the area of application are provided. The piperazine derivative deposited on the patient's skin is absorbed through the skin so that a filaricidal amount thereof is present in the dermal connective tissue of the patient. To enhance bioavailability, pH of the present compositions can be optimized for transdermal transport by incorporating therein a buffering agent and/or a mixture of the protonated and non-protonated forms of the piperazine derivative.

The topical composition of the present invention can also be used for prophylaxis. To this end, a filarial infection can be avoided, or at least the likelihood of such an infection can be substantially decreased, while living in or passing through an endemic region, by a regular application of a lotion, an ointment, an aerosol spray, or the like, containing the aforesaid piperazine derivative. Alternatively, a unit dosage form such as a water-permeable packet, wafer, or the like, containing a water-soluble form of the piperazine derivative can be regularly placed in the bath water to provide the desired prophylactic treatment.

The present invention is further illustrated by the following examples.

EXAMPLE I: Oral Treatment with Diethylcarbamazine (DEC)

Figure 1:
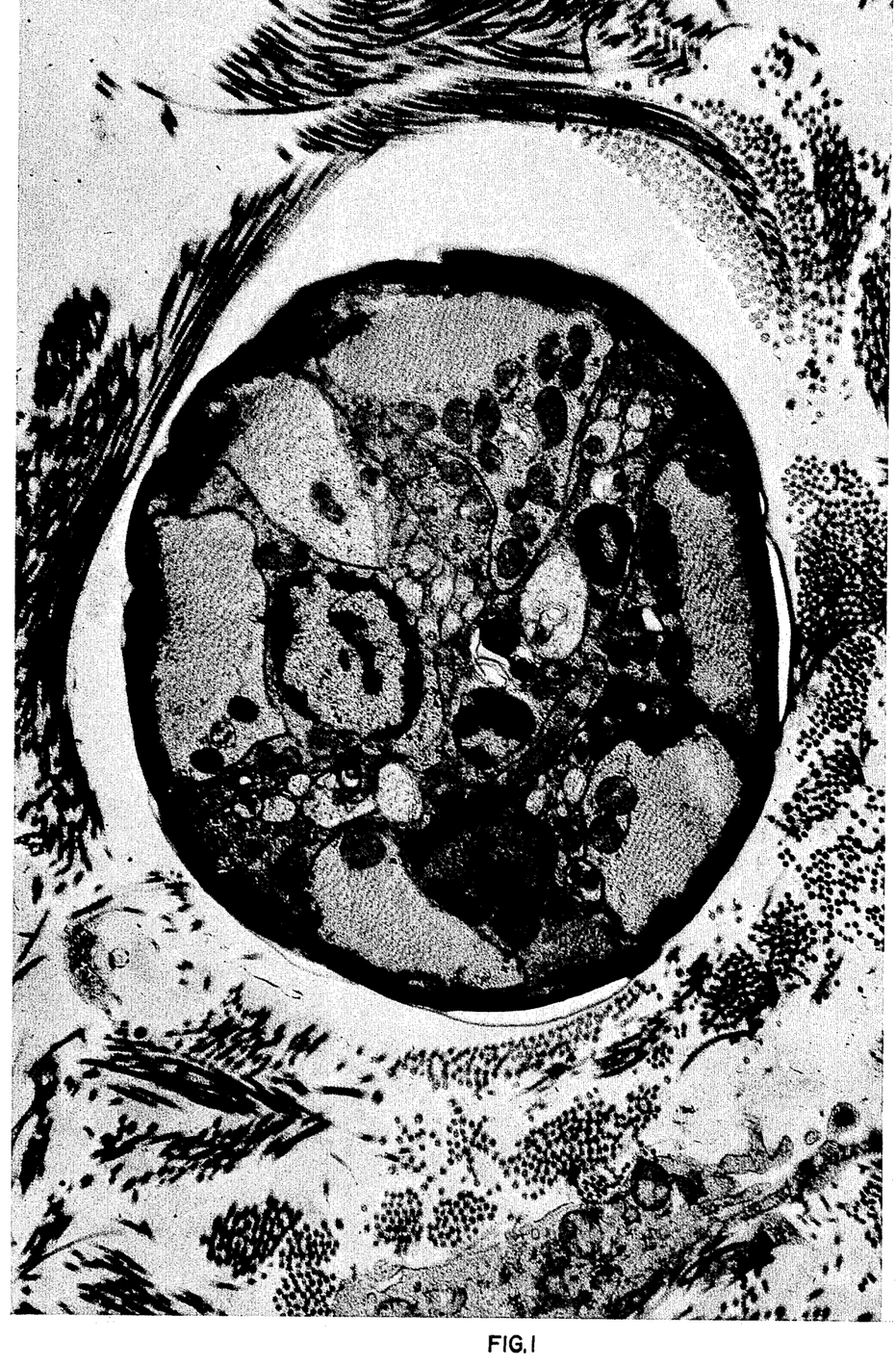
FIG. 1 is a photomicrograph showing internal structure of a microfilaria in a skin section taken from a skin sample of a young adult female patient afflicted with onchocerciasis.

A group of young adults with onchocerciasis were examined before and at periodic intervals after oral administration of 25 mg. DEC t.i.d. Standardized skin snips were removed using a Walser-type biopsy punch and upon examination revealed that the skin count of microfilaria per square millimeter ranged from 3 to 5 microfilariae. A typical section of skin containing a cross section of the microfilaria examined by electronmicroscopy at about 29,000× magnification is shown in FIG. 1.

The microfilariae are bordered by well developed, convoluted cuticles to which are attached the muscles which fill a large proportion of the body volume. In the immediate vicinity of the muscle fibrils are large numbers of mitochondria with well developed cristae. The microfilariae lie in the dermis and are surrounded by a narrow collagen-free space. No evidence of inflammatory response adjacent to the microfilariae was observed, but a variable degree of vasculitis was present in all patients. Histologically this was recognized by the presence of plasma cells within the dermis and, in particular, adjacent to the dermal capillaries. No dead microfilariae were found in the skin snips of 20 untreated patients that were examined histologically and electronmicroscopically.

Figure 2:
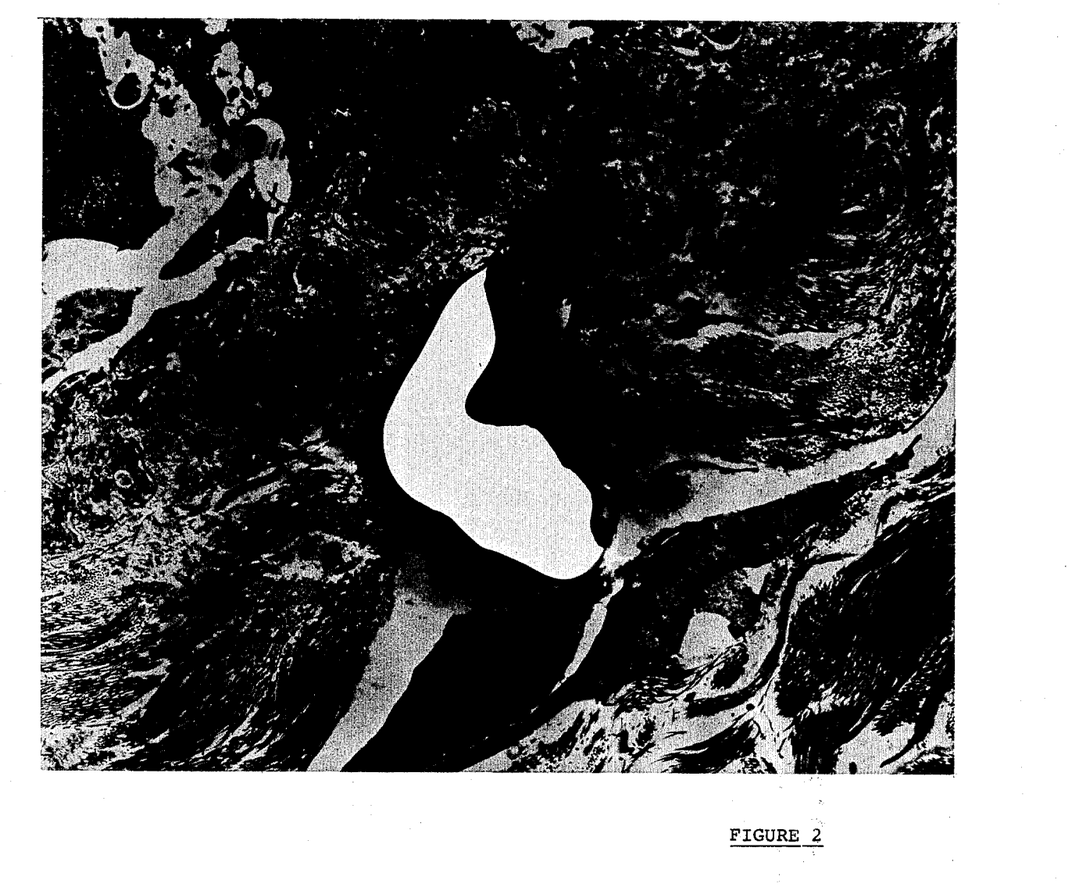
FIG. 2 is a photomicrograph showing internal structure of a dead microfilaria in a skin section taken from a skin sample of a young adult male patient afflicted with onchocerciasis, the skin sample having been taken 24 hours after oral administration of diethylcarbamazine (25 milligrams, t.i.d.)

One day after oral administration of DEC, both dead and live microfilariae were found in the skin examined histologically and electronmicroscopically. A representative electronmicroscopic cross section of a dead microfilaria in the skin at about 20,000× magnification is shown in FIG. 2. At this time the cuticles appeared intact; however, a complete breakdown of the internal organelles, which were replaced by large lipid-like bodies, was observed. These changes were found in areas of skin which showed a pruritic response to DEC (the Mazzotti response) and also in areas in which epithelial edema and subepithelial blisters formed on the infected skin. It was evident that in the former areas, death of the microfilariae had occurred prior to direct interaction with invading macrophages.

Continued oral administration of DEC for three weeks decreased the skin count of microfilariae, but histology and electronmicroscopy continued to reveal occasional live microfilaria. Three months after cessation of treatment, skin counts of microfilaria had partially or fully recovered and microfilariae were readily identifiable by histology and electronmicroscopy. During the period of DEC treatment, the vasculitis initially increased and then returned to its initial stage over the four month period.

EXAMPLE II: Topical Treatment with DEC in Wet Dressing

Figure 3:
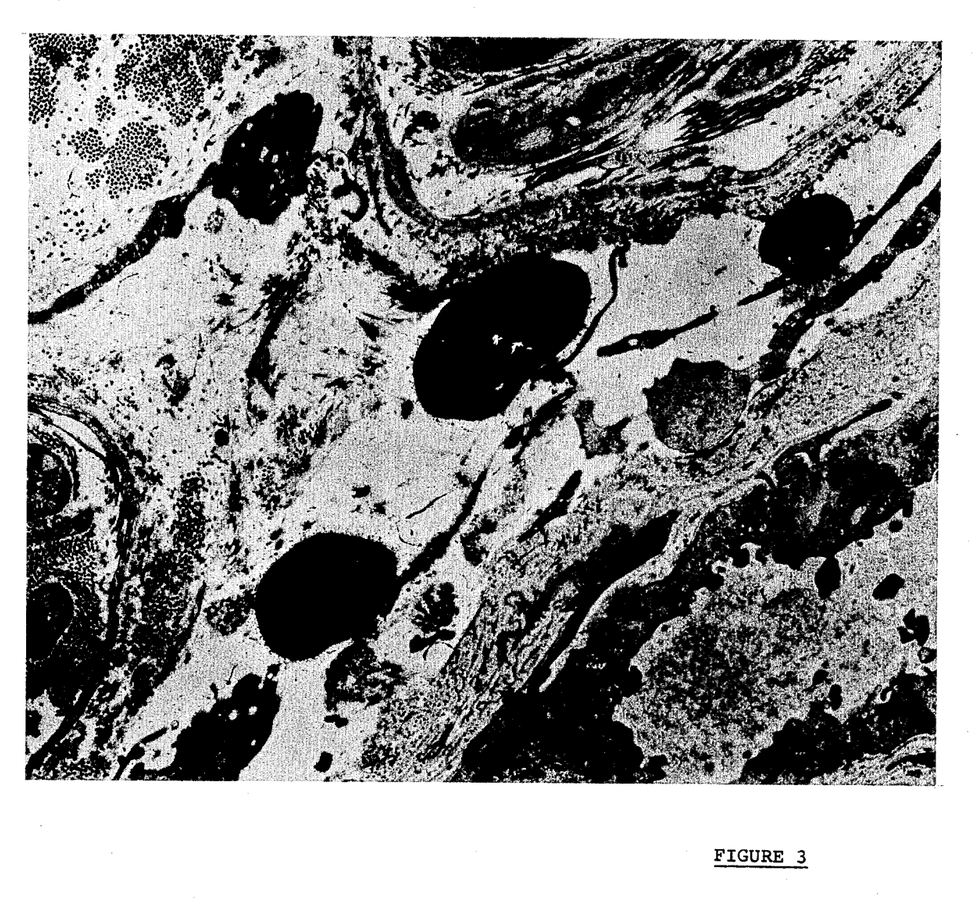
FIG. 3 is a photomicrograph showing internal structure of three segments of microfilariae in a skin section taken from a skin sample of an adult afflicted with onchocerciasis, the skin sample having been taken after two-hour topical administration of a 2-weight percent aqueous solution of diethylcarbamazine.

A circular piece of filter paper (about 5 cm diameter) was soaked with an aqueous solution of DEC (about 2 percent by weight), and the soaked filter paper was applied to an area of skin infected with microfilariae of *O. volvulus*. The application caused death of microfilariae in the underlying skin as shown at a magnification of about 10,600× in FIG. 3. The ultrastructural changes in the microfilaria shown in FIG. 3 are similar to the changes observable following an oral administration of DEC.

The microfilaricidal action was found to be closely restricted to the skin area covered by the filter paper. In some instances, but not always, death of the microfilariae was associated with localized itching.

EXAMPLE III: Topical Treatment by Immersion in an Aqueous Solution of DEC

Figure 4:
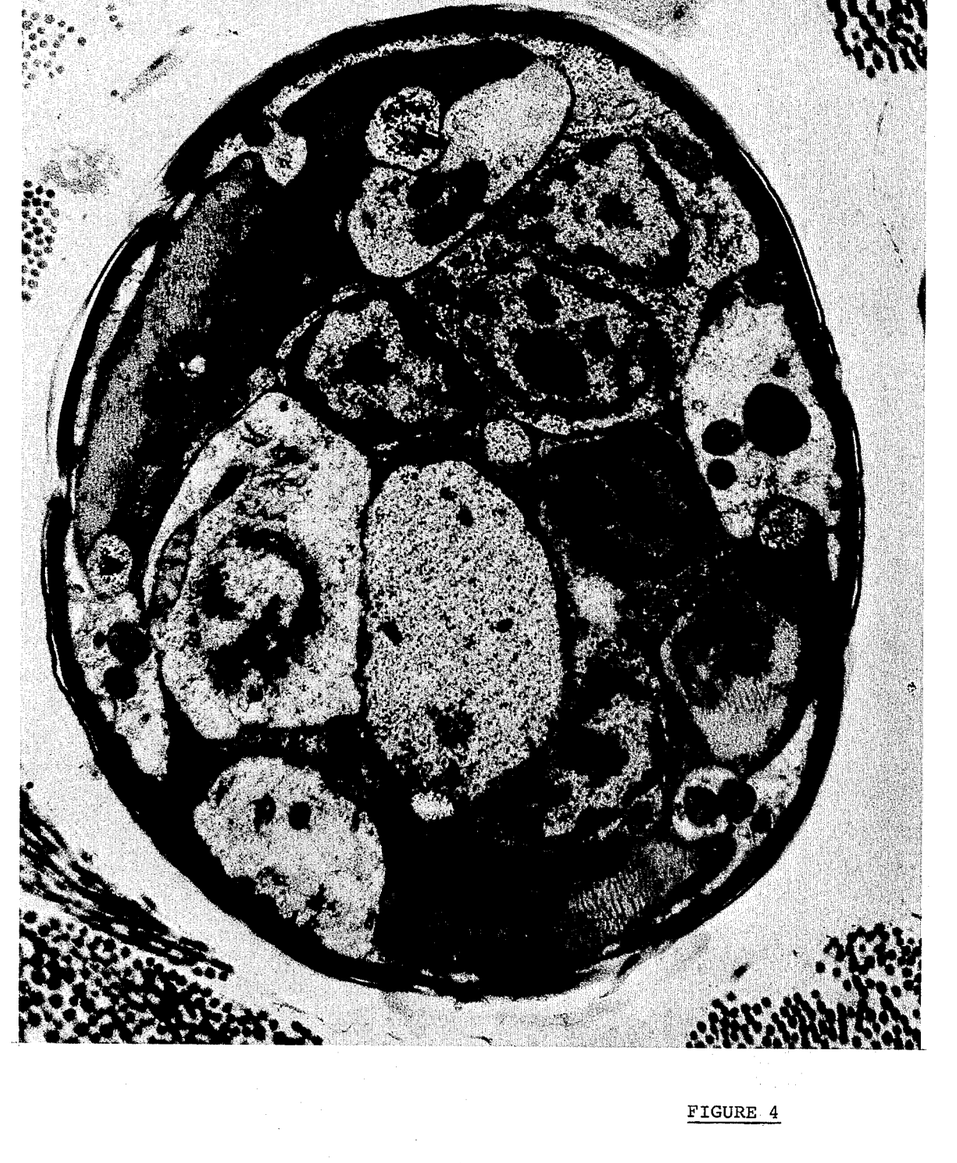
FIG. 4 is a photomicrograph showing internal structure of a microfilaria exhibiting early degenerative changes in a skin section taken from a skin sample of a young adult female afflicted with onchocerciasis after the patient was partially immersed for one hour in an aqueous bath containing diethylcarbamazine in a concentration of about 100 milligrams per 100 milliliters of bath solution, the skin sample having been taken from an immersed portion of the patient's body.

Patient were placed in an aqueous solution of DEC so that the body below the waist was exposed to the DEC solution. The aim of these studies was to determine the threshold concentration that would influence the microfilariae and to record the patient response. It was found that DEC concentrations as low as 20 milligrams/100 milliliters of solution led to definable changes in the ultrastructure of the microfilariae, but no death of these organisms was found. When a 0.1 percent by weight solution of DEC (100 milligrams/100 milliliters of solution) was used for an immersion period of about one hour, death of microfilariae occurred as can be seen at a magnification of about 39,000× from FIG. 4.

EXAMPLE IV: Topical Treatment Using DEC-Containing Lotion

Figure 5:
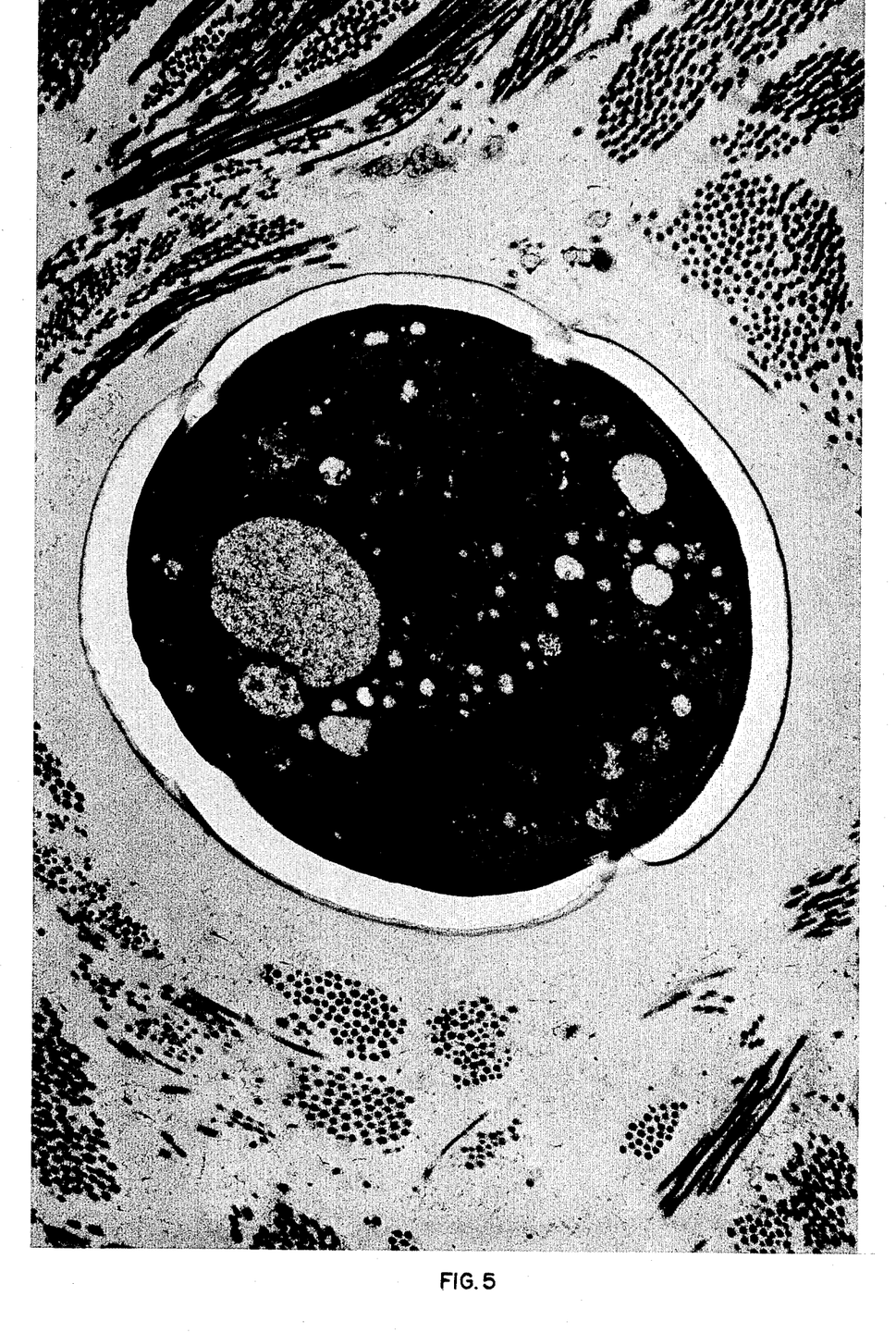
FIG. 5 is a photomicrograph showing internal structure of a microfilaria exhibiting first demonstrable degenerative changes in a skin section taken from a skin sample of a patient afflicted with onchocerciasis, the skin sample having been taken 24 hours after topical administration of an oil-in-water emulsion containing 1-weight percent diethylcarbamazine.
Figure 6:
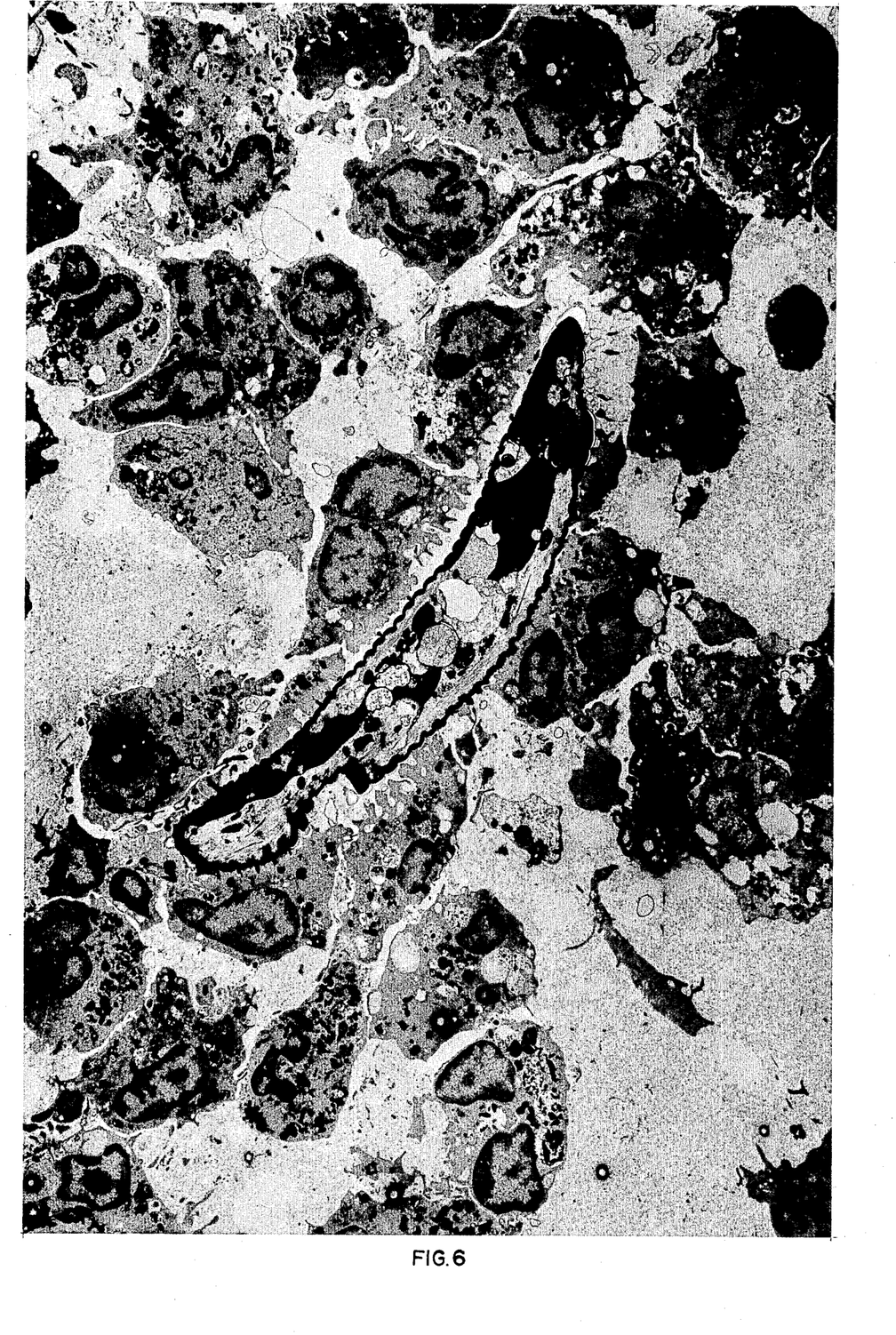
FIG. 6 is a photomicrograph showing internal structure of a dead and partially dissolved microfilaria in a skin section taken from a skin sample of a patient afflicted with onchocerciasis, the skin sample having been taken 24 hours after topical administration of an oil-in-water emulsion containing 1-weight percent diethylcarbamazine.

DEC was dissolved in an oil-in-water emulsion of the type commonly used as skin moisturizer lotion. DEC concentrations ranging from about 1 to about 5 percent by weight were applied to non-infected volunteers without apparent ill effect. Treatment of patients with onchocerciasis was simultaneously studied using the same range of DEC concentrations. The daily single application of a lotion containing 1 percent by weight of DEC, providing about 0.1 micrograms of the chemotherapeutic agent per square millimeter of patient's skin, to a group of 15 patients led to rapid death and complete breakdown of microfilariae. FIG. 5 shows at a magnification of about 36,000× degenerative stages of a microfilaria in a skin sample taken 24 hours after administration of the lotion, and FIG. 6 shows at a magnification of about 8,400× a dead and partially dissolved microfilaria in a skin sample taken 24 hours after administration of the lotion. By the fourth day of treatment the skin count of microfilaria had decreased to zero in all patients. These observations are summarized in Table I, below.

Table I

The Influence of 1-Percent by Weight DEC Lotion on the Number of Microfilariae in a Standardized Skin Snip

| Day | mf*/skin snip | Histology Pos. % |
|---|---|---|
| −2 | 15.8 ± 5.8 (15) | 100 (6) |
| 0 | 18.0 ± 7.4 (15) | 100 (4) |
| 2 | 0.7 ±0.4 (15) | 0 (3) |
| 4 | 0.0 ±0.0 (15) | 0 (4) |
| 70 | 0.0 ± 0.0 ( 5) | 0 (5) |

*microfilariae

The DEC lotion was applied on day 0 to 15 patients and again on days 1, 2 and 3. Five of these patients were given the same lotion to be reapplied once weekly, and the results on this group at day 70 are shown on the bottom line, supra. The numbers in parentheses represent the number of subjects examined.

In some patients, a pruritus developed and electronmicroscopy of skin snips taken from an affected area revealed marked inflammatory response; however, the subjective responses to the irritation of the inflammatory response appeared significantly less than to oral administration of the drug, and it was not necessary to institute antihistamine or cortical therapy. With the establishment of skin snips showing absence of microfilariae, the well-being of the patients improved significantly.

Electronmicroscopy examination of skin snips taken from patients treated with DEC lotion revealed a rapid breakdown of both the cuticle and internal organelles and complete disappearance of cell debris within a few days. A related finding to the treatment was the appearance in some treated patients of unicellular organisms within the dermis; these organisms were not present prior to the treatment, and it would appear that these organisms may have been present within the microfilariae.

The vasculitis in the patients treated with lotion intensified over the first few days of treatment.

Seven patients were given the same DEC lotion to reapply to their bodies once weekly. After ten weeks of treatment, skin snips were negative by the saline immersion procedure and by histology and electronmicroscopy. In one of the seven, vasculitis was absent, whereas it was still present in the other six patients. Reapplication of DEC lotion caused no skin reaction in any of the seven patients.

Treatment was discontinued after the fourth day in eight other patients. Five of these patients were seen again after 10 weeks. Three of the five had positive skin counts and microfilariae were confirmed by histology and electronmicroscopy; and the skin snips of the remaining two patients were negative. Application of DEC lotion to the five patients caused a minimal and localized skin Mazzotti response in two of the five subjects. One of these subjects was of especial interest as she had a well defined Onchocerca nodule on her left hip. The area adjacent to the nodule had been heavily infected, and the initial application of the DEC lotion resulted in marked pruritus in the lower half of the body. After the ten week period, the reapplication of the DEC lotion caused minimal skin reaction in the region of the nodule.

The foregoing results clearly establish that the transdermal application of a piperazine derivative characterized hereinabove in a carrier sucn as an aqueous solution or an oil-in-water emulsion provides an effective means of killing microfilariae of *O. volvulus*. This method provides an effective therapeutic means of eliminating microfilariae from the dermis over sustained periods of time. The clinical findings indicate that this method of treatment is significantly more effective than oral administration. On the practical level, the use of a lotion as the inert carrier for the drug has proven to be acceptable to the population of all ages in the endemic areas and results in less side reactions than are induced by oral administration of the drug. Moreover, the establishment of zero skin counts of microfilariae by the transdermal therapeutic approach described hereinabove provides a means for effectively breaking the Onchocerca biological cycle.

I claim:

1. A method of treating onchocerciasis which comprises topically administering to the skin of a human patient suffering from an infestation of Onchocerca volvulus a topical composition which comprises a dermatologically acceptable aqueous carrier suitable for topical application and having dispersed therein a piperazine derivative selected from the group consisting of a compound having the general formula wherein $R^1$ is a mamber of the group consisting of hydrogen and alkyl radicals containing 1 to 8 carbon atoms and $R^2$ and $R^3$ are members of the group consisting of hydrogen and alkyl radicals containing 1 to 8 carbon atoms, with the proviso that at least one of said $R^2$ and $R^3$ is said alkyl radical, and the corresponding physiologically tolerable acid addition salts thereof; said topical composition being administered to the skin of said patient in an amount sufficient to decrease the skin count of microfilariae of said *Ochocerca volvulus*.

2. The method in accordance with claim 1 wherein said carrier is water.

3. The method in accordance with claim 1 wherein said carrier is an aqueous emulsion.

4. The method in accordance with claim 1 wherein said carrier is an oil-in-water emulsion.

5. The method in accordance with claim 1 wherein said topical composition is administered as a wet dressing.

6. The method in accordance with claim 1 wherein said topical composition is administered as a lotion.

7. The method of treating onchocerciasis in accordance with claim 1 wherein said topical composition is administered in an amount sufficient to provide about 0.05 micrograms to about 0.25 micrograms of said piperazine derivative per square millimeter of said patient's skin in the area of application.

8. The method of treating onchocerciasis in accordance with claim 7 wherein said piperazine derivative is N,N-diethyl-4-methylpiperazine-1-carboxamide.

9. The method of treating onchocerciasis in accordance with claim 7 wherein said piperazine derivative is N,N-diethyl-4-methylpiperazine-1-carboxamide dihydrogen citrate.

10. The method of treating onchocerciasis in accordance with claim 7 wherein said piperazine derivative is N,N-diethyl-4-methylpiperazine-1-carboxamide hydrochloride.

11. The method of treating onchocerciasis in accordance with claim 1 wherein said topical composition is administered in an amount sufficient to provide about 0.1 micrograms of said piperazine derivative per square millimeter of said patient's skin in the area of application.

* * * * *